United States Patent [19]

Courbon

[11] Patent Number: 4,534,230
[45] Date of Patent: Aug. 13, 1985

[54] INDIVIDUAL PORTABLE DUST COLLECTOR

[75] Inventor: Paul Courbon, Apremont, France

[73] Assignee: Charbonnages de France, Paris, France

[21] Appl. No.: 519,244

[22] Filed: Aug. 1, 1983

[30] Foreign Application Priority Data

Aug. 3, 1982 [FR] France .................. 82 13541

[51] Int. Cl.³ ............................. G01N 1/24
[52] U.S. Cl. ..................... 73/863.23; 73/28
[58] Field of Search ............... 73/863.23, 28

[56] References Cited

U.S. PATENT DOCUMENTS

| | | | |
|---|---|---|---|
| 3,590,629 | 7/1971 | Courbon | 73/28 |
| 3,765,155 | 10/1973 | Courbon | 73/28 X |
| 3,949,594 | 4/1976 | Treaftis et al. | 73/28 |
| 4,152,923 | 5/1979 | Courbon | 73/28 |

FOREIGN PATENT DOCUMENTS

| | | |
|---|---|---|
| 733715 | 4/1943 | Fed. Rep. of Germany ... 73/863.23 |
| 2016032 | 10/1970 | Fed. Rep. of Germany . |
| 2039560 | 1/1971 | France . |
| 2086984 | 12/1971 | France . |
| 2082180 | 12/1971 | France . |
| 2389119 | 11/1978 | France . |
| 523334 | 7/1976 | U.S.S.R. ................ 73/28 |
| 840704 | 6/1981 | U.S.S.R. ................ 73/28 |
| 851075 | 7/1981 | U.S.S.R. ............ 73/863.23 |

OTHER PUBLICATIONS

Analytical Chemistry, vol. 48, No. 2, Oct. 1977 (Columbus, US) R. G. Lewis et al., "Evaluation of Polyurethane ...", pp. 1668–1672* p. 1668, colonne de droite, lines 23–27, FIG. 1*.

Ann. Occup. Hyg., vol. 24, No. 2, 1981 (Great Britain) Gibson, A. et al., "The Penetration of Dust ...", pp. 205–215.

Primary Examiner—Jerry W. Myracle
Assistant Examiner—Tom Noland
Attorney, Agent, or Firm—Cushman, Darby & Cushman

[57] ABSTRACT

An individual portable dust collector includes a ring of filter foam arranged to retain dust of a size in the range 5 microns to 0.5 micron. This ring is accommodated in a rotatable cup and has an exposed lateral surface located in a transverse plane. A cover surrounds the cup and has an air inlet orifice which is also located in said transverse plane. Outlet holes are provided in two diametrically opposed locations in said cover and are spaced from the transverse plane. A cowl caps the inlet orifice and contains a prefiltration block arranged to retain particles of a size greater than 5 microns.

10 Claims, 4 Drawing Figures

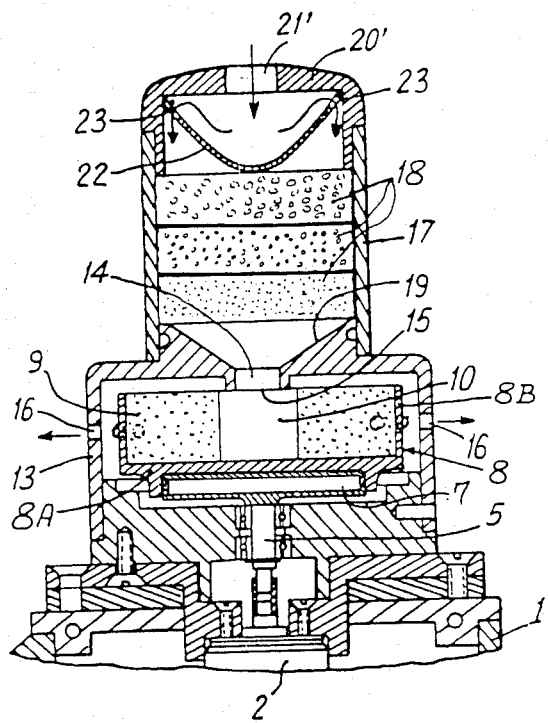

INDIVIDUAL PORTABLE DUST COLLECTOR

BACKGROUND OF THE INVENTION

The present invention relates to an individual dust collector.

The collector can be carried easily and can be used for taking samples of dust from the ambient atmosphere. Dust and particles of a size which can penetrate into the air-cells of a person's lungs is retained in the collector for subsequent analysis. Thus, it is possible to evaluate and even analyze the quality of breathable dust which a person is liable to inhale over a given period in various locations of an environment.

Apparatus for taking samples of dust from a polluted atmosphere are already known. For example, French Pat. No. 2,039,560 and its certificate of addition No. 2,082,180 describe apparatus in which a rotor made of filter material is rotated at a constant speed.

A device for the selective sampling of dust in a dusty atmosphere is also described in French Pat. No. 2,389,119.

These known devices are designed to be portable, that is to be sufficiently light-weight for a single person to be able to move them between two points, but generally they are too heavy to be carried permanently by this person during his activities. The weight of such known devices is typically of the order of 3 kg. Consequently, when it is used, the device is placed on the ground or is suspended, and is thus necessarily spaced from the precise and changing position where the person breathes during his activities.

Now it is expedient to have information which is as accurate as is possible about the quantity of breathable dust which a person could have inhaled over a given period of time. The known devices are not satisfactory in this respect, since it is known that the density of dust varies rapidly from place to place, and in particular from the place where the dust is generated, not far from where the person concerned is breathing, and the more distant and more sheltered place where the dust sampling device is located.

French Pat. No. 2,389,119 describes a device which is said to be capable of adaptation to a portable device. The present invention aims to provide an individual collector having a construction which is simpler than that of the device in this French patent and which has an at least equal efficiency. The present invention also seeks to provide a sufficiently lightweight device which is of a simple construction.

It is an object of the invention to provide a dust-collecting device which is as efficient as known devices, but is capable of being carried permanently by a person even while he is carrying out difficult or dangerous work. The device must thus be light-weight and of little bulk. As a result, the means provided on conventional devices for carrying out a classification of dust (for example, a cyclone) before it is collected are no longer acceptable.

SUMMARY OF THE INVENTION

According to the invention there is provided a portable dust collector comprising a rotatable cup having a bottom and a side wall extending from said bottom and a ring of filter foam accommodated in said cup, said ring having a central channel, a cover surrounding said cup, said cover having a central air inlet and a lateral air outlet, and a cowl supported on said cover, said cowl having an air passage which caps the central air inlet of the cover, wherein the cowl is filled with at least one prefiltration block and has a duct arranged after said block in the direction of air flow and connected to said central air inlet of the cover, said inlet ending at an outlet orifice which has a smaller diameter than that of the central channel of the filter foam ring, the inlet being coaxial with said channel, and wherein the thickness of the foam ring is equal to the height of the side wall of the cup, the foam ring having a substantially exposed lateral surface which is located in a transverse plane and faces said air inlet.

The outlet orifice of the duct preferably has a smaller dimension than that of the central channel of the foam ring. The outlet orifice is preferably located in a transverse plane which is the plane in which the exposed lateral surface of the foam ring is located.

The cover has air-outlet holes located on two diametrically opposed sides thereof and distributed in two opposite angular sectors. These sectors preferably each have a spread of approximately 80°.

The air-outlet holes are advantageously located in a transverse plane which is spaced in the direction of the bottom of the cup relative to the transverse plane of the exposed lateral surface of the foam ring. The spacing is, for example, 45 to 50% of the thickness of the foam ring.

The cowl is preferably perforated with at least one hole through its end face directly opposite the prefiltration block in the direction of the circulation of air through the latter.

In a preferred embodiment, the cowl contains a single prefiltration block consisting of filter foam of grade 45 and the ring is made of filter foam of grade 80 or 100.

Alternatively, it is possible to arrange within the cowl several successive prefiltration blocks in series, the blocks having increasingly fine grades. The cowl may also contain a concave deflector, the concave bottom of which is located opposite at least one central hole which extends in the end face of the cowl and the periphery of which has several spaced apertures opening opposite the prefiltration block.

BRIEF DESCRIPTION OF THE DRAWINGS

Embodiments of the present invention will hereinafter be described, by way of example, with referance to the accompanying drawings, in which:

FIG. 4 is a partial longitudinal section of a collector as in FIG. 1 but showing a modification containing a plurality of prefiltration blocks.

DESCRIPTION OF PREFERRED EMBODIMENTS

Figure 1:
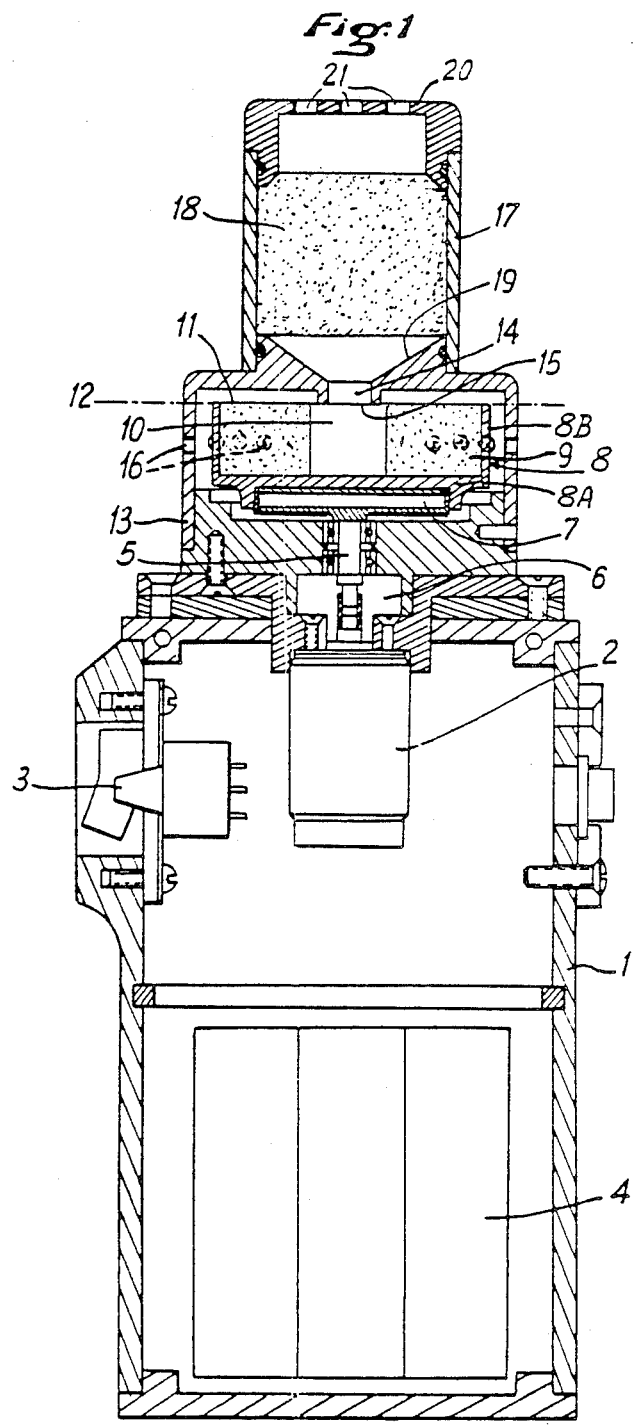
FIG. 1 is a longitudinal section of an individual portable collector according to the invention.

An individual portable dust collector of the present invention is illustrated in FIG. 1 and comprises a hollow body 1 in which a motor 2 is housed. A cut-off switch 3 for the motor 2 is arranged laterally of the body 1. An electrical power source 4 is also housed within the body 1 underneath the motor 2. In use, a shaft 5 of the motor 2 extends vertically upwardly through a bearing 6 and ends in a magnetised plate 7. A cup 8 which has a bottom 8A and a side wall 8B adheres to the plate 7 such that the cup 8 is rotated upon rotation of the shaft 5 and hence of the plate 7. The entire volume of the cup 8 contains a ring 9 which consists of filter foam and has a central channel 10. The height of the side wall 8B, or the depth of the cup 8, is identical to the thickness of the foam ring 9. Thus, when the ring 9 is accommodated in the cup 8 a completely exposed lateral surface 11 of the ring 9 is located in a transverse plane 12 which is indicated by a dot-dash line and which is also the plane in which the annular end face of the side wall 8B is located. The surface 11 faces towards the inflow of the air to be filtered, but it does not encounter by the arriving air as will be understood better at a later stage.

The rotary assembly which has just been described is enclosed in a cover 13 removably fastened to the body 1. This cover 13 has a central air inlet 14, the diameter of which is less than the diameter of the central channel 10 of the foam ring 9. As is clearly illustrated, the central air inlet 14 ends at an outlet orifice 15 which is equal in diameter to the inlet 14 and is coaxial to the central channel 10. Advantageously, the outlet orifice 15 is located in the transverse plane 12. The cover 13 also has an air outlet defined therein. In the embodiment shown this outlet comprises two rows of holes 16 extending through the side wall of the cover in diametrically opposed locations, one on the left and the other on the right as seen in FIG. 1. Each row of holes 16 extends over a sector of approximately 80°. All the holes 16 are in a transverse plane which is offset from the transverse plane 12. The spacing between the plane containing the holes 16 and the transverse plane 12 is of the order of half the thickness of the foam ring 9.

Of course, the two rows of holes 16 could be replaced by two slots or two perforated areas of the side wall of the cover 13 if preferred.

Mounted on the cover 13 is a cowl 17 having an air passage and capping the central air inlet 14. This cowl 17 contains at least one prefiltration block 18 formed of filter foam and having a diameter greater than that of the central air inlet 14. Between the block 18 and the air inlet 14 is a duct 19, for example a convergent duct, which communicates with the air inlet 14 and is connected to it. In fact, in this embodiment, the duct 19, and the central channel 14 and the outlet orifice 15 are all formed in the cover 13 which thus houses the entire junction. On the other side of the block 18 of filter foam, the cowl 17 has a transverse end wall 20 through which several longitudinal air-inlet holes 21 extend. These holes 21 open directly opposite the block 18 in the direction of the passage of air through the latter.

Figure 2:
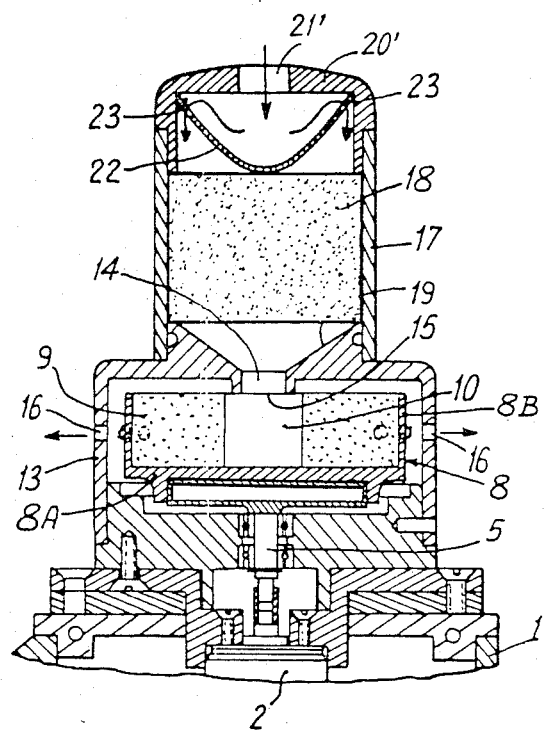
FIG. 2 is a partial diagrammatic view of an alternative cowl for a collector as shown in FIG. 1.

In an alternative embodiment of the portable collector which is illustrated in FIG. 2, the cowl 17 terminates in a transverse end wall 20' which has a longitudinally extending central hole 21' communicating with the concave bottom of an inner concave deflector 22. This deflector is arranged upstream of the block 18 in the direction of air flow, and has several spaced apertures 23 in its periphery. Air sucked into the hole 21' as a result of rotation of the cup 8 arrives, as indicated by arrows, in a central axial stream, follows the deflector radially, and then forms several peripheral axial streams guided directly to the prefiltration block 18.

In normal use, the prefiltration block 18 would consist of open-pored foam, for example, of grade 45 (which means that it has 45 cells per linear inch or 45 cells per length of 25.4 mm), whilst the ring 9 would consist of open-pored foam, for example, of grade 80 or 100 (which means that it has 80 or 100 cells per length of 25.4 mm).

Constructed in this way, the collector has a filtration cut-off of the order of a particle size of 5 microns. The largest particles are retained in the prefiltration block 18, whilst those capable of being retained in the lungs, that is having a size in the range 5 microns to 0.5 micron, are retained in the foam ring 9. The finest particles escape from the collector via the holes 16. However, as these holes 16 are located on two opposite sides, as shown in both FIGS. 1 and 2, the collector can be carried on the chest or hung round the neck or on the shoulder of a user.

It is possible to vary the filtration cut-off, for example, by using a different grade foam for the prefiltration block 18. Thus, it is possible to modify the filtration cut-off to comply with existing standards. In particular, instead of selecting a cut-off corresponding to a particle size of 5 microns, it can be set at a different value such as, for example, 7 or 10 microns.

The alternative form of the cowl 17 illustrated in FIG. 2 is useful in an atmosphere which contains larger particles or fairly large particles in great quantities. These larger particles are retained to a substantial extent in the bottom of the concave deflector 22. It would also be possible to place in the deflector 22 a block of filter foam which retains only the largest particles.

It is possible to replace the prefiltration block 18 with several successive prefilters of decreasing porosity (that is to say, of increasing grade), as shown in FIG. 4, in order to separate and collect several separate layers of decreasing particle size and at the same time conduct a brief analysis of the dimensions of the dust.

Because the size of the particles retained not only depends on the porosity (or grade) of the foam, but also on the velocity of the gas passing through it (a higher velocity being accompanied by the retention of smaller grains), it is also possible to vary the diameter of the prefilters, for example by surrounding them with a solid ring of greater or lesser thickness within the cowl 17, to produce various prefiltration layers above the dimension of 5 microns.

In a test using the collector described and illustrated, the velocity of the gas was 0.35 m/s and the motor was rotating at 7,000 revolutions per minute, and air was sucked in at a rate of approximately 600 liters per hour. The prefilter had a diameter of 25 mm and a thickness of 20 mm, and the ring 9 had an outside diameter of 35 mm.

Figure 3:
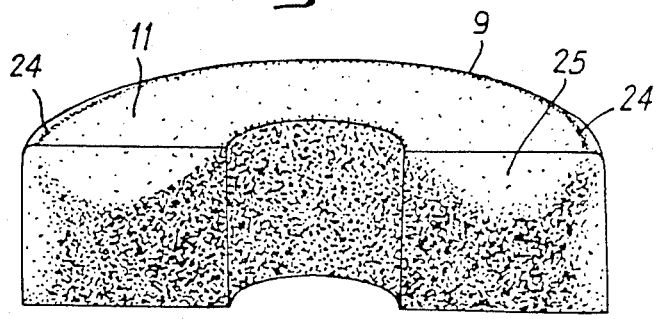
FIG. 3 is a view in diametral cross-section and in perspective of a foam ring after the collector of FIG. 1 has been used.

FIG. 3 shows, in diametral cross-section, a ring 9 consisting of filter foam of grade 80, the exposed lateral face 11 being seen slightly from above and in perspective. The air stream laden with dust of 5 microns and less, which flows out of the orifice 15, is distributed substantially over the entire height of the ring 9 and the cup 8. The air is expelled radially as a result of centrifugal force and abandons any dust having a particle size greater than 0.5 micron, the air then flows out via the exposed face 11, following a narrow annular strip 24 along the side wall 8B of the cup 8 and passing round a central semi-toroid 25 cut by the lateral face 11. This annular strip 24 must always remain exposed on the face 11. The profile of the central semi-toroid 25 depends on the component between the axial velocity of the air stream at the outlet of the orifice 15 after it has been concentrated by the convergent duct 19 and the rotational speed of the cup 8 and the ring 9 of filter foam.

Accurate weighing, before and after use, of the cup 8 containing the foam ring 9 or of the foam ring 9 alone gives the weight of the dust retained by the collector.

I claim:

1. A portable dust collector comprising a rotatable cup having a bottom and a side wall extending from said bottom, a ring of filter foam accommodated in said cup said ring having a central channel, a cover surrounding said cup, said cover having a central air inlet and a lateral air outlet, and a cowl supported on said cover, said cowl having an air passage which caps the central air inlet of the cover, wherein the cowl is filled with at least one prefiltration block and has a duct arranged after said block in the direction of air flow and connected to said central air inlet of the cover, said inlet ending at an outlet orifice which has a smaller diameter than that of the central channel of the filter foam ring, the inlet being coaxial with said channel, and wherein the thickness of the foam ring is equal to the height of the side wall of the cup, the foam ring having a substantially exposed lateral surface which is located in a transverse plane and faces said air inlet.

2. A collector according to claim 1, wherein the outlet orifice of said air inlet is located in said transverse plane in which the lateral surface of the foam ring is located.

3. A collector according to claim 1, wherein the air flows out of the cover by way of holes extending through a side wall of the cover in two diametrically opposite locations arranged in a further transverse plane spaced from said transverse plane.

4. A collector according to claim 3, wherein the spacing of the further transverse plane from said transverse plane is a distance of the order of 45% to 50% of the thickness of the foam ring.

5. A collector according to claim 1, wherein the cowl has an extreme end wall and at least one hole extends therethrough, said hole or holes extending in the direction of air flow towards the prefiltration block.

6. A collector according to claim 5, wherein the cowl has several spaced longitudinal holes which open directly opposite the prefiltration block.

7. A collector according to claim 5, wherein the cowl has at least one longitudinal central hole which opens opposite the concave bottom of a concave deflector which is located upstream of the prefiltration block, and wherein spaced longitudinal apertures are provided in the peripheral zone of said concave deflector and open directly opposite the prefiltration block.

8. A collector according to claim 7, wherein the deflector contains a prefiltration foam block arranged to retain particles of a size greater than a predetermined value.

9. A collector according to claim 1, wherein several successive prefiltration blocks of decreasing porosity are housed in said cowl, such that the blocks retain particles of a size greater than a predetermined value, and wherein said ring is of filter foam arranged to retain particles of a size between said predetermined value and 0.5 micron.

10. A collector according to claim 1, the cowl contains a prefiltration block arranged to retain particles having a size greater than 5 microns, and said ring consists of filter foam arranged to retain particles having a size between 5 microns and 0.5 micron.

* * * * *